US00PP16119P2

(12) United States Plant Patent
McLaren

(10) Patent No.: US PP16,119 P2
(45) Date of Patent: Nov. 15, 2005

(54) APRICOT TREE, 'F194 CV'

(50) Latin Name: *Prunus armeniaca*
Varietal Denomination: 'F194 cv'

(75) Inventor: John McLaren, Cromwell (NZ)

(73) Assignee: Nevis Fruit Company USA LLC, Boulder, CO (US)

( * ) Notice: Subject to any disclaimer, the term of this patent is extended or adjusted under 35 U.S.C. 154(b) by 107 days.

(21) Appl. No.: 10/845,647

(22) Filed: May 14, 2004

(51) Int. Cl.[7] ..... A01H 5/00
(52) U.S. Cl. ..... Plt./186
(58) Field of Search ..... Plt./186

*Primary Examiner*—Anne Marie Grunberg
(74) *Attorney, Agent, or Firm*—Wells St. John P.S.

(57) ABSTRACT

A new and distinct variety of apricot tree is disclosed and which is mature for harvesting and shipment under the ecological conditions prevailing in Eastern Washington, about August 15$^{th}$.

4 Drawing Sheets

BACKGROUND OF THE NEW VARIETY

The present invention relates to a new and distinct variety of apricot tree, *'Prunus armeniaca'*, and which has been denominated varietally as 'F194 cv' hereinafter, and more specifically to a new apricot tree variety which is characterized as to novelty by bearing large, light orange-colored fruit which have some pinkish red blush. This new variety of apricot tree is also notable for producing fruit which are ripe for harvesting and shipment at least about 3 weeks later than other common apricot varieties such as "Perfection" (not patented) under the ecological conditions prevailing in Eastern Washington.

ORIGIN AND ASEXUAL REPRODUCTION

The present variety of apricot tree was originated by me from a cross which I conducted between the unpatented apricot varieties "Sundrop" with a late "Moorpark" variety in 1987. I conducted this cross at my orchard which is located in Central Otago, New Zealand. The present variety showed noteworthy characteristics and was selected in 1992. Following selection, I grafted test trees for further observation. Since that original selection, nine generations of fruit have been observed on the original tree, and later in test plantings of second-generation trees which have been grafted onto various peach, apricot and plum rootstocks. Regardless of the rootstock type selected, all subsequently asexual reproduced trees, and the fruit produced thereby, appeared to be substantially identical, and true to type to the originally selected tree. Budwood of the present variety was sent to the quarantine facility, IR-2, at Prosser, Wash. for further testing for virus. Virus-free material was later released in 1997, and was budded into a test orchard located in Orondo, Wash. These subsequent test trees, in that same test orchard, have been continually observed, and have further demonstrated that the characteristics of the present tree are true to the original selection.

SUMMARY OF THE VARIETY

The new variety of apricot tree, 'F194 cv' is characterized as to novelty, and is otherwise deemed noteworthy by producing fruit which ripen for commercial harvesting and shipment approximately August 15$^{th}$ under the ecological conditions prevailing in Orondo, Wash. This harvesting date has been observed to be at least three weeks later than that observed of the "Perfection" and "Moorpark" apricot trees which ripen approximately in the same season. In relative comparison to the Sundrop apricot tree, the present variety 'F194 cv' produces fruit which ripen about 47 days later under the ecological conditions prevailing in my orchard in New Zealand. Further, in relative comparison to the late Moorpart apricot tree, the present variety produces fruit which are ripe for harvesting and shipment about 36 days later than the Moorpark apricot tree under the same ecological conditions.

BRIEF DESCRIPTION OF THE DRAWINGS

The accompanying drawings are color photographs of various aspects of the present plant. The colors are as nearly true as is reasonably possible in color representations of this type. Due to chemical development, processing and printing, the leaves and fruit of the present tree may, or may not be, accurate when compared to the actual specimen. For this reason, future color references should be made to the color plates as provided by the Munsell Book of Color, and the other general color descriptions as provided for hereinafter.

DETAILED DESCRIPTION

Figure 1:
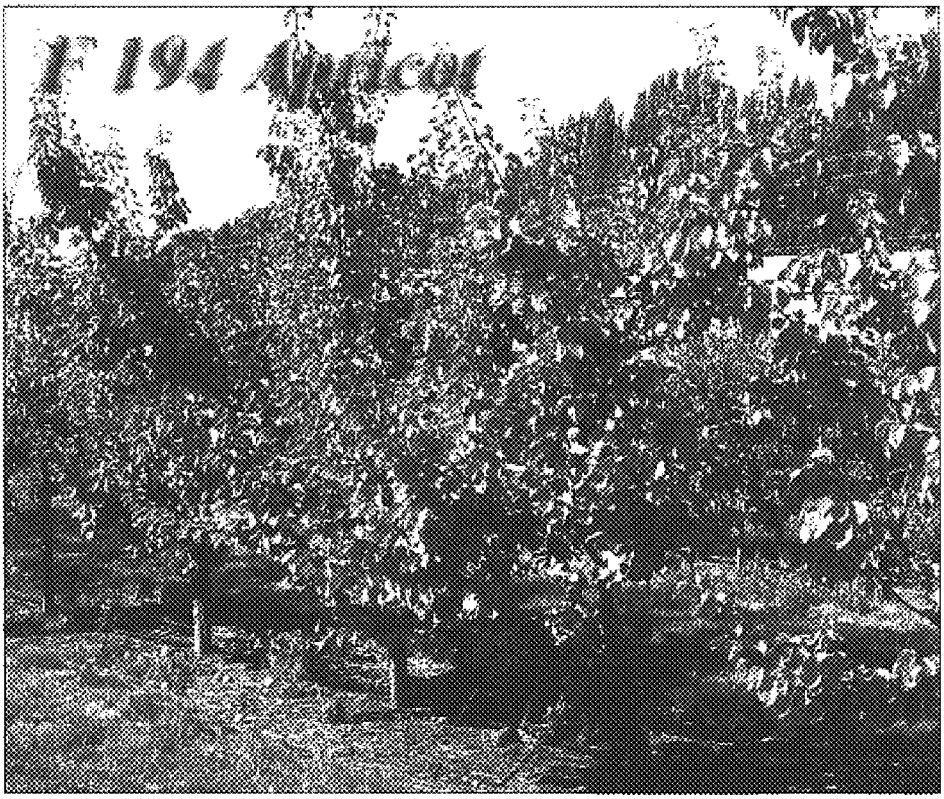
FIG. 1 shows the growing habit of five-year-old trees of the new variety of apricot tree as presently growing in during the 2003 growing season.
Figure 2:
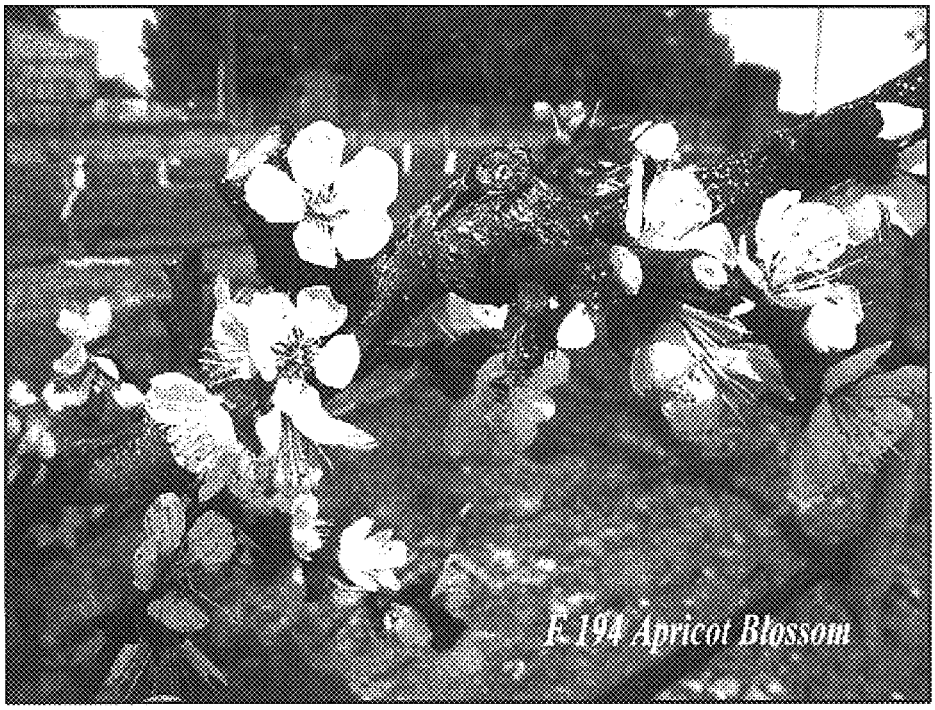
FIG. 2 shows the blossom characteristics of the present variety of apricot in full bloom and as seen on Apr. 20, 2003.
Figure 3:
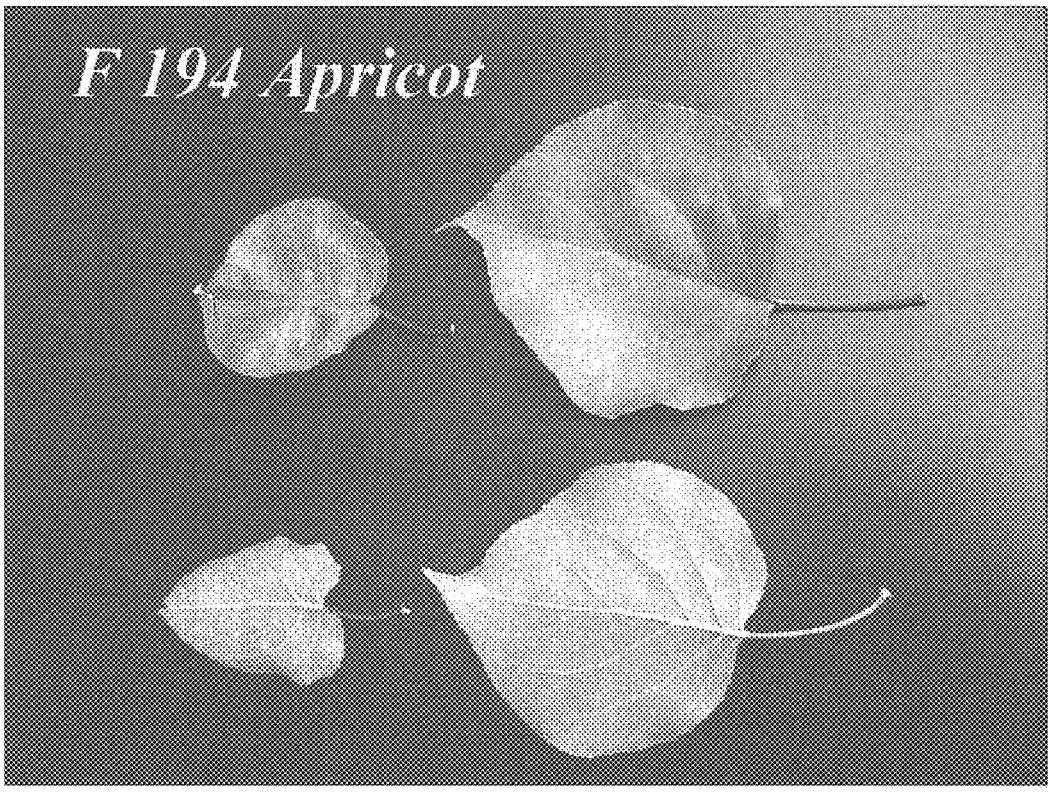
FIG. 3 shows the dorsal and ventral surfaces of both young (left) and mature (right) leaves of the new variety of apricot tree.
Figure 4:
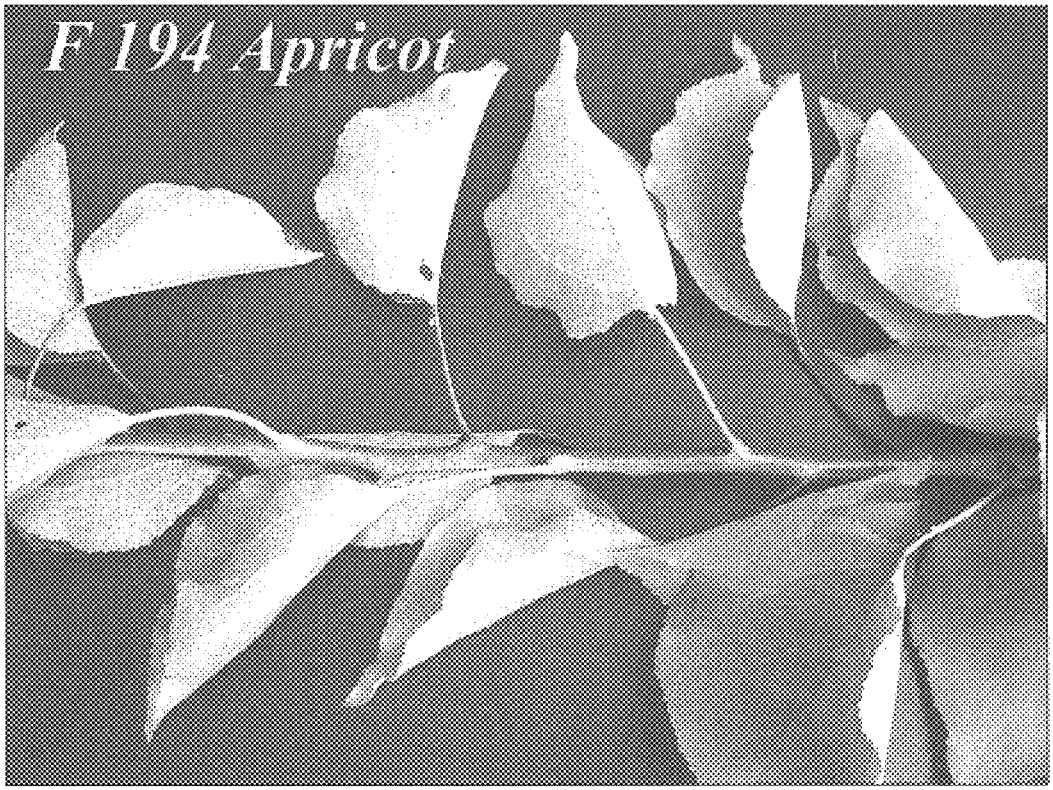
FIG. 4 illustrates the characteristics of a typical current season shoot with its associated leaves.
Figure 5:
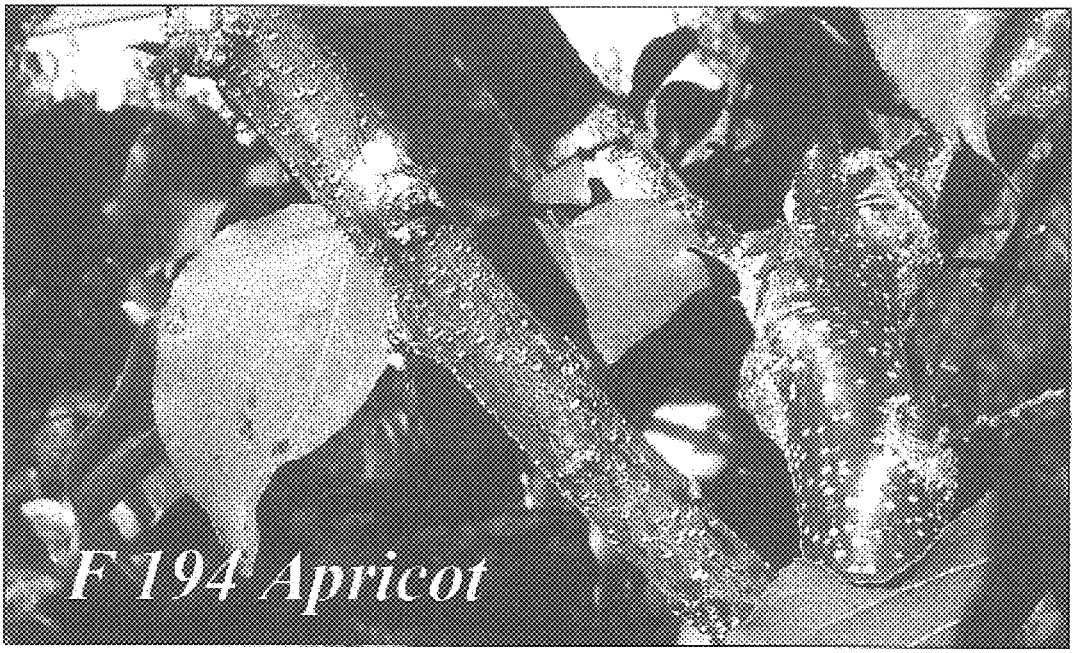
FIG. 5 illustrates the characteristics of both second and third year wood currently growing on a test tree.

Referring more specifically to the pomological details of this new and distinct variety of apricot tree, the following has been observed during the 2003 growing season under the ecological conditions prevailing in an orchard located near Orondo, Wash. All major color code designations are by reference to the Munsell Book of Color. Common color names are also used occasionally.

TREE

Tree size: Considered average, Fourth leaf trees (four years in the field) have a height of about 3 to about 4 meters; and a width of about 2 to about 3 meters.

Productivity: Considered average. About 3 to about 4 kg. of fruit per tree were harvested on trees in their fourth leaf.

Vigor: Considered vigorous. The present variety shows about 1 to about 1½ meters of annual growth. All current test trees are grafted onto "Manchurian" apricot rootstock.

Growing habit: Considered spreading.

Chilling requirement: The chilling requirements of the present variety of apricot tree appears to be similar to other common commercial apricot varieties based upon the observation of these same trees as grown in the orchard of the inventor in New Zealand; and in the state of Washington. Actual chilling requirements for the subject tree have not been precisely determined.

Regularity of bearing: Considered regular and uniform.

TRUNK

Size: Considered average for this variety. The present tree was about 5 cm. in diameter when measured at a distance of about 0.3 meters from the surface of the ground.

Bark color: Brown and having an orange tint, (7.5 YR 5/10).

Lenticels:

*Color*.—Light tan (7.5 YR 8/4).

BRANCHES

Growth habit: Generally considered spreading, and normally having new, vigorous vertically oriented shoots.

Bark color:

*New growth*.—Green (2.5 GY 4/6), and later becoming a shade of purple (7.5 R 3/6). The bark color at full maturity is brown (7.5 YR 4/4).

Pubescence: None is observed.

Lenticels:

*Numbers*.—Typically 8 to 12 lenticels are found per square cm.

Lenticels:

*Shape*.—Elongated and having a width dimension of about 0.5 mm.; and a length dimension of about 2 mm.

Lenticels:

*Color*.—Tan (10 YR 7/4).

Internodes:

*Length*.—Considered average and about 1 to about 2 cm.

LEAVES

Leaf size: Generally considered average. Mature leaves have a length dimension of about 5 to about 8.9 cm. and a width dimension of about 5.2 to about 8.1 cm.

Leaf form: Generally considered to be a typical apricot leaf. In this regard, the leaf appears somewhat rounded, and having a lanceolate tip and an obtuse base. The base appears to be oriented at substantially about 90 degrees relative to the leaf petiole.

Leaf margin:

*Form*.—Considered wavy and reflexed upward relative to the midrib of same.

Leaf color:

*Dorsal surface*.—Light green (2.5 GY 7/8).

Leaf color:

*Ventral surface*.—Light grey-green (2.5 GY 7/4).

Leaf color:

*Mid vein*.—Considered reddish purple (2.5 R 3/10).

Marginal form: Considered finely to coarsely crenate. The number of crenations are approximately 5 per cm.

Mid-vein thickness: About 1.5 mm.

Leaf glandular characteristics: Typically 1 to about 4 glands appear, and often these glands are in pairs, and are seen on the upper surface of petiole. The glands on average are about 1 mm. in diameter.

Stipules: None observed.

Leaf petiole:

*Size*.—Considered average for the variety, about 3 to 4 cm. in length; and about 1 to about 2 mm. in diameter.

Leaf petiole:

*Color*.—Considered reddish purple (2.5 R 3/10).

FLOWER

Time of bloom: Date of full bloom was observed on Mar. 22, 2003 under the prevailing ecological conditions existing near Orondo, Wash. First Bloom was observed on Mar. 18, 2003. Petal fall was observed on Mar. 28, 2003. The flower has no detectable fragrance.

Flower buds:

*Size*.—Dormant flower buds have a width dimension of about 1.5 mm.; and a length dimension of about 3.5 mm.

Flower buds:

*Surface texture*.—Considered glabrous with tightly overlapping scales.

Flower buds:

*Color*.—Dormant flower buds have a brown color (2.5 YR 2/4). Just prior to opening, (considered the popcorn stage), the flower buds have a light pink color (2.5 R 9/2).

Size of flower: On average, about 20 to 30 mm in diameter.

Flower petals:

*Length*.—About 15 to 16 mm.

Flower petals:

*Width*.—About 10 to about 12 mm.

Flower petals:

*Color*.—Light pink at the popcorn stage (2.5 R 9/2). The petals have a white color when the flower is fully opened.

Sepals:

*Color*.—Considered bright red (5 R 4/14).

Stamens:

*Numbers*.—About 14 to about 20 are observed per flower.

Stamens:

*Length*.—About 8 to about 12 mm.

Filaments:

*Numbers*.—About 25 are observed per flower.

Filaments:

*Length*.—About 10 mm.

Anthers:

*Color*.—Yellow (5 Y 5/12).

Pistil:
*Length*.—About 15 mm.
Stigma:
*Length*.—About 1 mm.

FRUIT

Generally, the fruit produced by the present variety of apricot tree is described as it will be found at full commercial maturity. In this regard, the fruit of the present variety was ripe for harvesting under the ecological conditions prevailing near Orondo, Wash. on Aug. 15, 2003. This harvesting date is considered at least about 3 weeks later than the harvesting date for the "Perfection" and "Moorpark" apricot trees (unpatented) at the same geographical location.

Fruit size: Considered large for the variety. The average weight of the harvested fruit was about 102.3 grams.
Fruit form: Somewhat variable, and considered elliptical to round. This form is similar to the fruit produced by the "Perfection" apricot tree.
Suture: Considered prominent. The suture extends from the stem to the stylar scar, and is about 1 mm to about 2 mm in depth. The suture of the present variety is considered to be much more prominent, in relative comparison, to that seen on the fruit produced by the "Perfection" apricot tree.
Skin color: Considered a Pale orange (7.5 YR 7/12). Occasionally a pinkish-red blush (5 R 5/10) and some speckling may be observed.
Pubescence: Present. This pubescence is very fine, and soft, and has no apparent sheen.
Skin cracking: The variety does not display any apparent skin cracking over the shoulder region at commercial maturity.
Ripening characteristics: Considered uniform. This characteristic is similar to that of the fruit produced by the "Perfection" apricot tree, but is unlike the fruit produced by the "Moorpark" apricot tree which typically ripens in an uneven manner.
Flesh color: Orange (7.5 R 7/14).
Flesh texture: Considered juicy, melting, and non-fibrous.
Flesh flavor: Considered very good, and comparable to the fruit produced by the "Moorpark" apricot tree. Still further, the flesh of the present variety of apricot tree appears to have a lower acidity in relative comparison to the fruit produced by the "Perfection" apricot tree.
Fibers: Not observed.
Aroma: Wanting.
Eating quality: Considered well above average.

STONE

Figure 6:
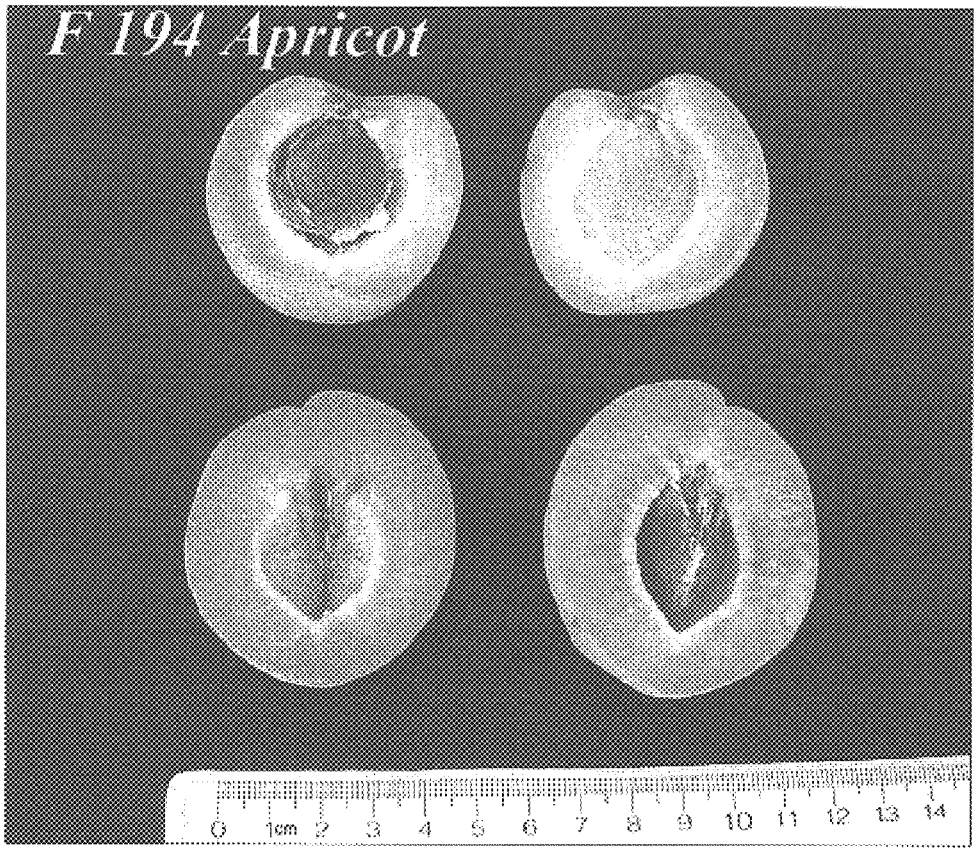
FIG. 6 illustrates several mature fruit of the present variety which have been dissected in the longitudinal and transverse planes and which shows the flesh and stone characteristics, thereof.
Figure 7:
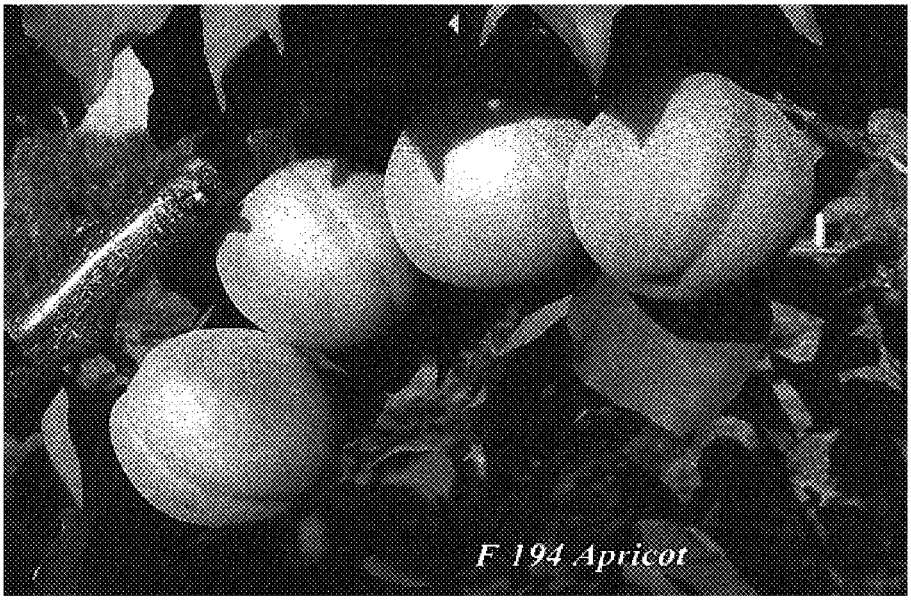
FIG. 7 illustrates the fruit of the present variety of apricot tree at a stage of development where it is sufficiently matured for harvesting and shipment.

Attachment: Generally considered free stone. The stone adheres to the flesh only along the ridges thereof. As seen in the drawings (FIG. 6), an air gap may be present in the region of the flesh immediately adjacent to the stone.
Stone size: Considered medium to large.
Stone length: About 30 mm.
Stone width: About 27 mm.
Stone thickness: About 15 mm.
Stone form: Somewhat variable, and considered oblong to oval. The stone has a prominent sharp center ridge and secondary ridges which are subordinate thereto. These secondary ridges are located in a region where there is a primary attachment to the flesh.
Base shape: Rounded.
Apex shape: Rounded.
Stone side-shape: Considered substantially equal.
Ridges-form: Three sharp medium sized ridges are normally observed.
Stone surface texture: Considered average, that is, somewhat smooth.
Surface color: A dull Brown (7.5 YR 5/8).
Pit color: Light tan (7.5 YR 7/6).
Pit-form: Considered plump, and further having a bitter, strong, almond flavor. The pit has a very hard shell.
Intended use: The present variety appears to be useful for the commercial market.
Disease and insect resistance: No susceptibilities were noted.
Keeping quality: Considered good, the present variety has been kept in cold storage for as long as 3 weeks.

Although the new variety of apricot tree possesses the described characteristics as a result of the growing conditions prevailing in Eastern Washington, it is to be understood that variations in the usual magnitude and characteristics incident to growing conditions, fertilization, pruning and pest control are to be expected.

Having thus described and illustrated my new variety of apricot tree, what I claim is new and desire to secure by Plant Letters Patent is:

1. A new and distinct variety of apricot tree substantially as illustrated and described and which produces fruit which are mature for harvesting and shipment about August $15^{th}$ under the ecological conditions prevailing in Eastern Washington, and which further has an attractive pale orange skin color, which has an occasional pinkish-red blush.

* * * * *